United States Patent
Muller et al.

(10) Patent No.: US 7,816,537 B2
(45) Date of Patent: Oct. 19, 2010

(54) PROCESS FOR THE MANUFACTURE OF EPOXYBUTANOL INTERMEDIATES

(75) Inventors: Marc Muller, Wolfersdorf (FR); Lin Xu, Shanghai (CN)

(73) Assignee: Basilea Pharmaceutica AG, Basel (CH)

( * ) Notice: Subject to any disclaimer, the term of this patent is extended or adjusted under 35 U.S.C. 154(b) by 204 days.

(21) Appl. No.: 12/085,617

(22) PCT Filed: Nov. 29, 2006

(86) PCT No.: PCT/CH2006/000671
§ 371 (c)(1),
(2), (4) Date: May 28, 2008

(87) PCT Pub. No.: WO2007/062542
PCT Pub. Date: Jun. 7, 2007

(65) Prior Publication Data
US 2009/0299073 A1    Dec. 3, 2009

(30) Foreign Application Priority Data
Dec. 1, 2005    (EP)    ................... 05026163

(51) Int. Cl.
C07D 301/32    (2006.01)
C07D 303/14    (2006.01)
C07D 249/08    (2006.01)
C07D 277/24    (2006.01)

(52) U.S. Cl. .................... 548/205; 548/262.2; 549/540; 549/559; 549/560

(58) Field of Classification Search ........................ None
See application file for complete search history.

(56) References Cited

FOREIGN PATENT DOCUMENTS

| | | |
|---|---|---|
| EP | 1083175 | 3/2001 |
| EP | 1535914 | 6/2005 |
| WO | WO 99/45008 | 9/1999 |
| WO | WO 99/52840 | 10/1999 |

OTHER PUBLICATIONS

International Search Report and Written Opinion dated Sep. 11, 2007.

*Primary Examiner*—Kamal A Saeed
*Assistant Examiner*—Michael Barker

(57) ABSTRACT

Disclosed is a process for the manufacture of a compound of formula (I)

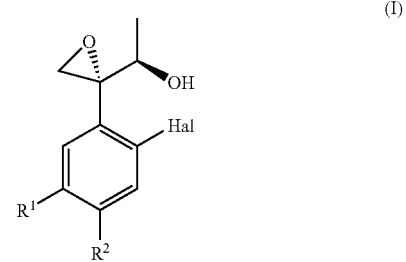

wherein
Hal represents fluoro or chloro, and $R^1$ and $R^2$ represent, independently from one another, hydrogen or Hal; in which process a compound of formula (II)

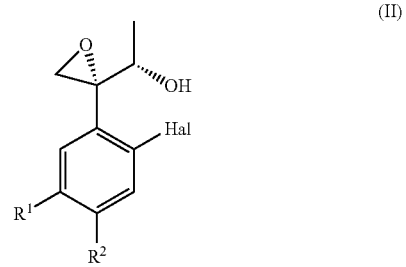

is converted to a corresponding alkyl, fluoroalkyl or aryl sulfonic acid ester, which is then reacted with an alkali metal nitrite in the presence of a suitable crown ether in a polar non-nucleophilic solvent at a temperature of −10 to 50° C. to give the compound of formula (I).

17 Claims, No Drawings

PROCESS FOR THE MANUFACTURE OF EPOXYBUTANOL INTERMEDIATES

The present invention relates to a process for the manufacture of (2R,3R)-3-(halogenophenyl)-3,4-epoxy-2-butanol derivatives which are useful in the synthesis of azole antifungal compounds like e.g. (1R,2R)-4-[2-[2-(2,4-Difluoro-phenyl)-2-hydroxy-1-methyl-3-[1,2,4]triazol-1-yl-propyl]-thiazol-4-yl]benzonitrile or, in particular, (1R,2R)-4-[2-[2-(2,5-Difluoro-phenyl)-2-hydroxy-1-methyl-3-[1,2,4]triazol-1-yl-propyl]-thiazol-4-yl]-benzonitrile (BAL 4815) and to a process for manufacturing such azole antifungal compounds using the aforementioned process.

BACKGROUND OF THE INVENTION

Processes for the preparation of (2R,3R)-3-(halogenophenyl)-3,4-epoxy-2-butanol derivatives are known in the art. The known processes usually start from the rather costly R-lactic acid or D-(−)-lactic acid. For example, US 2003/0236419 A1 discloses a process for manufacturing (2R,3R)-3-(2',4'-difluorophenyl)-3,4-epoxy-2-butanol wherein D-methyl lactate is converted to (2R)-2',4'-difluoro-2-hydroxy-propiophenone, which is then reacted with trimethyloxosulfonium bromide/sodium hydride to give a 12:1-mixture of (2R,3R)-3-(2',4'-difluorophenyl)-3,4-epoxy-2-butanol and the corresponding (2R,3S)-compound. A similar reaction is described in WO99/45008 for manufacturing (2R,3R)-3-(2',5'-difluorophenyl)-3,4-epoxy-2-butanol.

WO 9952840 A1, on the other side, discloses the use of the much less expensive S-lactic acid (L-(+)-lactic acid) instead of R-lactic acid as the basic starting material for (2R,3R)-3-(2',4'-dihalogenophenyl)-3,4-epoxy-2-butanol derivatives. It is, however, necessary to change the configuration of carbon atom 2 of the butanol skeleton in course of said process in order to arrive at the desired R-configuration at said carbon atom. This is achieved according to WO 9952840 A1 via the well-known Mitsunobu Reaction, wherein the intermediate (2S,3R)-3-2',4'-dihalogenophenyl)-3,4-epoxy-2-butanol derivative is reacted with p-nitrobenzoic acid in the presence of triphenylphosphine and diethylazodicarboxylate (DEAD) to give (2R,3R)-3-(2',4'-dihalogenophenyl)-3,4-epoxy-2-butanol p-nitrobenzoic acid ester, which is then saponified to the corresponding butanol derivative.

Said Mitsunobu Reaction step however has several disadvantages, in particular if is to be applied on a technical scale. It provides only unsatisfactory yields of the desired (2R,3R) derivative, produces an unacceptable quantity of waste, and said process step is only difficult up-scalable, if at all, because substantial problems with the purification of the product arise at a larger scale.

In particular, If the classical Mitsunobu conditions, disclosed in WO 9952840 A1 in connection with the manufacture of (2R,3R)-3-(2',4'-difluorophenyl)-3,4-epoxy-2-butanol, is applied to the respective 2',5'-difluoro analog, an unsatisfactory yield of only about 50% can be obtained. Moreover, the enantiomeric excess observed is only about 90%, hence no full conversion reversal is achieved.

It has now been found, however, that using instead a specific alternative of the Mitsunobo step in the manufacture of (2R,3R)-3-(halogenophenyl)-3,4-epoxy-2-butanol provides much better yields, and has not the disadvantages associated with said reaction step.

SUMMARY OF THE INVENTION

A first subject of the present invention is therefore a process for the preparation of a compound of formula (I)

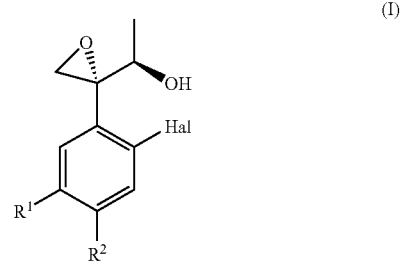

(I)

wherein
Hal represents fluoro or chloro, and
$R_1$ and $R^2$ represent, independently from one another, hydrogen or have one of the meanings of Hal;

in which process a compound of formula (II)

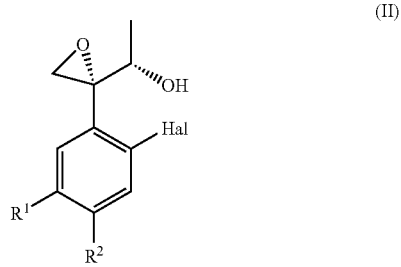

(II)

is converted to a corresponding alkyl, fluoroalkyl or aryl sulfonic acid ester, which is then reacted with an alkali metal nitrite in a polar non-nucleophilic solvent at a temperature of minus 10° C. to 50° C. and in the presence of a suitable crown ether, to give the compound of formula (I).

Suitable alkyl or aryl sulfonic acid esters include for example p-toluene sulfonic acid ester, methyl sulfonic acid ester and in particular trifluoromethyl sulfonic acid ester. The conversion of the compound of formula (II) to the corresponding alkyl or aryl sulfonic acid esters can be accomplished in a way known per se, e.g. by reacting the compound of formula (II) with an alkyl or aryl sulfonic acid halide, e.g. the chloride, or preferably the anhydride in the presence of a base like e.g. pyridine, preferably at temperatures between minus 10° C. and 50° C., more preferably between minus 10° C. and 10° C., e.g. at 0° C., in a non-polar solvent like e.g. methylene chloride. The ratio of alkyl or aryl sulfonic acid derivative, e.g. the respective halide or anhydride, in particular the trifluoromethylsulfonic acid anhydride, and the compound of formula (II) is preferably between 1:1 and 3:1, more preferably between 1.5:1 and 2.5:1. The base, e.g. pyridine, is used in about the same quantities as the alkyl or aryl sulfonic acid derivative. Suitable reaction times range from about 15 minutes to several hours, e.g. 10 hours, preferably from 1 to 3 hours.

After optional purification of the reaction product and/or removal of the solvent, the alkyl, fluoroalkyl or aryl sulfonic acid ester of the compound of formula (II) is dissolved in a polar non-nucleophilic solvent like, for example, dimethylsulfoxide (DMSO), N,N-dimethylformamide (DMF), 1,3-dimethyl-3,4,5,6-tetrahydro-2(1H)-pyrimidinone (DMPU), tetrahydrofurane (THF), dioxane or formamide, and is reacted with an excess of an alkali metal nitrite, e.g. sodium, potassium or caesium nitrite, in the presence of a suitable crown ether as catalyst.

DETAILED DESCRIPTION OF THE INVENTION

Preferably a two- to tenfold excess of the alkali metal nitrite is used, more preferably a four- to sixfold excess. Suitable crown ethers can be readily chosen by those skilled in the art, mainly depending on what alkali metal nitrite is applied, and include 18-crown-6-ether, 15-crown-5-ether, 12-crown-4 ether. 18-crown-6-ether is specifically preferred, in particular when used with potassium nitrite. As mentioned, it is used in catalytical amounts, e.g. in an amount ranging from a thousandth to a tenth part of the molar quantity of the alkali metal nitrite. The reaction is preferably carried out at about 10 to 30° C., more preferably at about 15 to 25° C., e.g. at room temperature.

After completion of the reaction, the mixture is preferably treated with diluted aqueous sodium hydroxide, preferably for a time period of about one hour. Then the compound is preferably extracted with an appropriate solvent or solvent mixture. The solvents used include e.g. ethyl acetate, linear or branched $C_{5-8}$ alkanes, methyl acetate, ethyl acetate which is especially preferred, propyl acetate, and symmetric or asymmetric dialkyl ethers, the alkyl groups of which comprise from 1 to 5 carbon atoms. After extraction and appropriate washing (brine) the compound (I) can be used as is, directly without further purification required.

Particularly preferred embodiments of the process according to the present invention accordingly include a process as described above wherein the compound of formula (II) is converted to the trifluoromethylsulfonic acid ester and then further processed. Furthermore preferred is the process of the present invention, wherein the alkali metal nitrite is sodium or, more preferably, potassium nitrite, as well as the process of the invention, wherein the crown ether is the 18-crown-6 ether when potassium nitrite is used and 15-crown-5-ether when sodium nitrite is used. In a further preferred embodiment of the aforementioned process, dimethylsulfoxide (DMSO), N,N-dimethylformamide (DMF), 1,3-dimethyl-3, 4,5,6-tetrahydro-2(1H)-pyrimidinone (DMPU), Tetrahydrofurane (THF), dioxane or formamide, in particular DMF, are used as the polar non-nucleophilic solvent, or suitable mixtures of said solvents.

A further preferred embodiment is a process of the present invention for manufacturing compounds of formula (I), wherein Hal represents fluoro, and one of $R^1$ and $R^2$ represents hydrogen and the other fluoro, in particular if $R^1$ represents fluoro and $R^2$ hydrogen. By the way of example, in case of manufacturing (2R,3R)-3-(2',5'-difluorophenyl)-3,4-epoxy-2-butanol, yields of about 80% and more can be achieved with the process of the present invention, with no other diastereoisomers being detected, whereas the standard Mitsunobu reaction yields only about 50% as already mentioned above.

The compounds of formula (II) can, in general, be obtained according to the following Reaction Scheme 1:

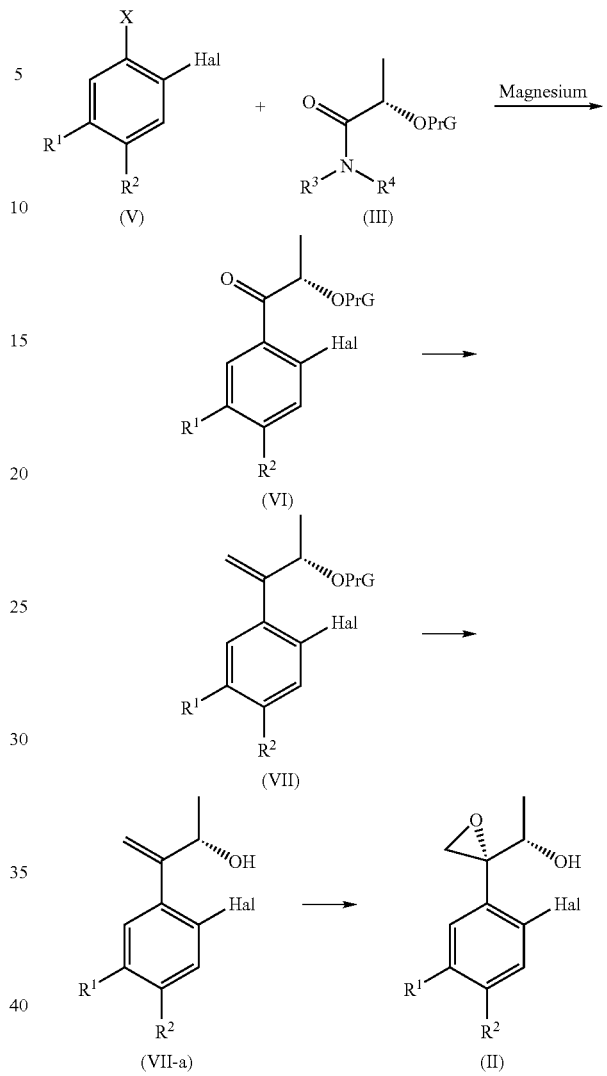

The compound of formula (VI) can, for example, be manufactured by reacting a compound of formula (V), wherein Hal represents fluoro, or chloro more preferably fluoro, and $R^1$ and $R^2$ represent, independently from one another, hydrogen or fluoro, or chloro, more preferably fluoro, and X is Iodo or preferably bromo, with magnesium in a suitable organic solvent like THF and in a manner known per se to form the magnesium bromide of the compound of formula (V); i.e. said compound wherein X represents MgBr. This compound is then further reacted with the compound a formula (III), wherein PrG represents a hydroxyl-protecting group like e.g. benzyl, trityl, methoxymethyl, 1-ethoxy-ethoxyl, methoxyethoxymethyl, SiMe$_3$, SiEt$_3$ SiMe$_2$tBu, SiPh$_2$Me, COMe, COEt, COiPr, COBu, COsecBu, COtBu, or, in particular, 2-tetrahydropyranyl, $R^3$ represents methyl or ethyl, and $R^4$ represents methyl, ethyl or methoxy (Weinreb amide), or $R^3$ and $R^4$ taken together with the nitrogen atom to which they are bound represent a 4- to 6-membered heterocyclic group having either no or one or two further heteroatoms selected from nitrogen or oxygen; e.g. like e.g. a pyrrolidine, imidazolidine, pyrazolidine, piperazine or, in particular, morpholine residue. A preferred compound of formula (III) is (2S)-1-Morpholin-4-yl-2-(tetrahydropyran-2-yloxy)-propan-1- one (which can be obtained, for example, as described in Chem. Pharm. Bull. 41, 1035, 1993). The reaction is preferably performed at a temperature between minus 10° C. and room temperature, i.e. 20° C. to 25° C. over about 1 to 10 hours, preferably 3 to 8 hours. A preferred solvent for this reaction is THF.

The compound of formula (VI) can, for example, be converted to a compound of formula (VII) by reacting compound of formula (VI) with methyl triphenyl-phosphonium bromide and lithium bis(trimethylsilyl)amide, preferably in amounts of 1 to 2 mole equivalent per mole of the compound of formula (VI), in a suitable solvent like THF, a dialkyl ether, dioxane, DMF or DMSO. Suitable reaction temperatures range from about minus 70° C. to 50° C. Reaction times are generally between 1 to 24 hours, preferably between 1 and 15 hours.

The compound of formula (VII-a) can be obtained by reaction of the compound of formula (VII) with about 0.1 to 1 mole of pyridinium-p-toluenesulfonate per mole of the compound of formula (VII) in an alcohol as solvent, preferably methanol, ethanol or propanol, during about 1 to 24 hours, preferably 1 to 10 hours, and at a temperature ranging from 0 to 60° C. preferably 30° C.

The compound of formula (II) is enantioselectively obtainable from a compound of formula (VII-a) via the well-known Sharpless Epoxidation route, i.e. the reaction of the compound of formula (VII-a) with about 1 to 5 mole of t-butyl hydroperoxide (TBHP) per mole of the compound of formula (VII-a) in the presence of about 0.1 to 1, preferably about 0.5, mole titanium(IV) isopropoxide (TIPO) per mole of the compound (VII-a) and 0.1 to 1, preferable 0.3, mole of a dialkyl L(+)-tartrate, preferably L(+)-diethyl tartrate. Preferred solvents for said reaction include chloroform and particularly methylene chloride, to which molecular sieve powder (about 3 to 4 angstroms) is added. Suitable reaction temperatures range from minus 30 to room temperature (20 to 25° C.), preferable from about minus 25 to about 10° C., suitable reaction times range between 5 and 20 hours, e.g. 8 to 15 hours.

In a further aspect the present invention relates also to a process for the manufacture of a compound of formula (IV-a).

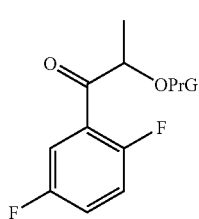

(IV-a)

wherein PrG represents a hydroxyl-protecting group,

In which process 1,4-difluorobenzene is reacted in the presence of a base with a compound of formula (III-a)

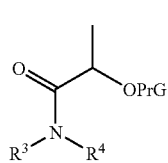

(III-a)

wherein

PrG has the same meaning as in Formula (IV-a).

$R^3$ represents methyl or ethyl, and $R^4$ represents methyl, ethyl or methoxy, or $R^3$ and $R^4$ taken together with the nitrogen atom to which they are bound represent a 4- to 6-membered heterocyclic group having either no or one or two further heteroatoms selected from nitrogen or oxygen.

PrG, $R^3$ and $R^4$ have preferably the same meaning as indicated already above, most preferably PrG represents a tetrahydropyran-2yl residue and $R^3$ and $R^4$ taken together with the nitrogen atom to which they are bound represent a morpholin-4-yl group.

Suitable bases for use in said reaction include strong bases like amid bases, e.g. lithium hexamethyldisilazane (LiHMDS), sodium hexamethyldisilazane (NaHMDS) or potassium hexamethyldisilazane (KHMDS), lithiumdiisopropylamine (LDA), butyllithium (BuLi), or sodium tert-butylate (KOtBu) and the like and mixtures thereof, the most preferred base being LDA.

Suitable as solvents are, in general, aprotic, inert solvents like e.g THF or dioxane.

The compound of formula (III) is preferably added at relatively low temperatures during said process, and the reaction temperature ranges preferably from minus 78° C. to 15° C. Particularly suitable reaction temperatures are about 10° C.

The aforementioned process is particularity suitable for manufacturing the (2S,3R)-3-2',5'-difluoro)-3,4-epoxy-2-butanol of formula (II-b according to the following Reaction Scheme 1-a) and it allows to start with 1,4-difluorobenzene which must not be converted beforehand to 1-bromo-2,5-difluorobenzene as would be the case when using the Grignard route described above.

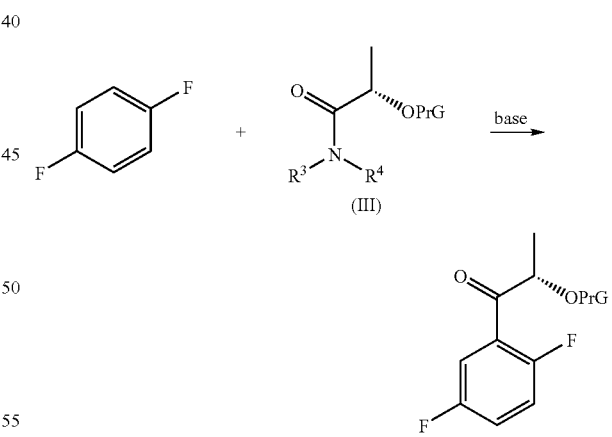

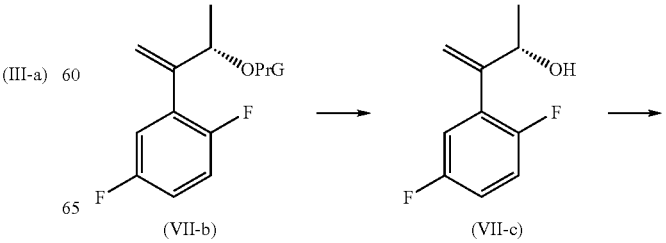

-continued

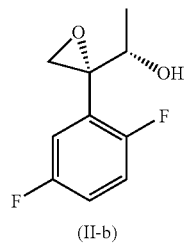

(II-b)

This reaction cannot be used with 1,3-difluorobenzene as the starting material because with this compound alkylation almost quantitatively takes place in the 2-position i.e. between the two fluoro substituents.

For synthesis of azole antifungal compounds like (1R,2R)-4-[2-[2-(2,4-difluoro-phenyl)-2-hydroxy-1-methyl-3-[1,2,4]triazol-1-yl-propyl]-thiazol-4-yl]-benzonitrile or, in particular, (1R,2R)-4-[2-[2-(2,5-difluoro-phenyl)-2-hydroxy-1-methyl-3-[1,2,4]triazol-1-yl-propyl]-thiazol-4-yl]-benzonitrile the intermediates of formula (I) must be further processed.

In a special embodiment of the process according to the present invention the compound of formula (I) as obtained in the process of claim 1 is therefore reacted with 1,2,4-triazole in the presence of a base to give a compound of formula (VIII)

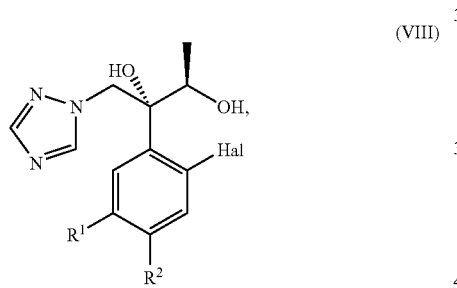

(VIII)

wherein Hal, $R^1$ and $R^2$ have the same meaning as in formula (I), and said compound is then converted to a compound of formula (IX):

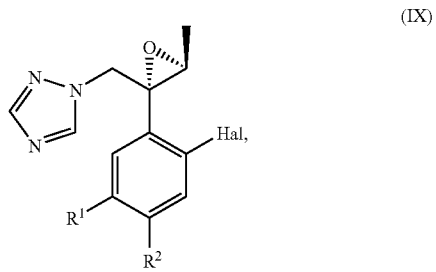

(IX)

wherein Hal, $R^1$ and $R^2$ have also the same meaning as in formula (I).

This reaction is described, for example, in WO99/45008. The compound of formula (I) is e.g. reacted with a two to fivefold excess of 1,2,4-triazole in the presence of a base like sodium hydride in a dry suitable solvent like DMF or DMSO at a temperature between 50 and 100° C. for about 1 to 12 hours, preferably 2 to 5 hours. The obtained compound of formula (VIII) is optionally purified and is then reacted in a suitable solvent like e.g. methylene chloride with methylsulfonium chloride in the presence of an organic base like pyridine or trimethylamine for 0.5 to 5 hours at a temperature of minus 10 to 10° C., e.g. about 0° C. Then a base, like NaOH or NaOMe is added to perform the epoxy ring formation, and the epoxy product is preferably purified.

In a particularly preferred embodiment of the process of the present invention the compound of formula (IX) is further converted to a compound of formula (X)

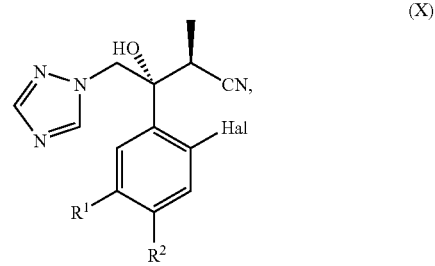

(X)

wherein Hal, $R^1$ and $R^2$ have the same meaning as in formula (IX), and said compound of formula (X) is then reacted with dithiophosphoric acid O,O-diethyl ester or ammonium sulfide to give a compound of formula (XI):

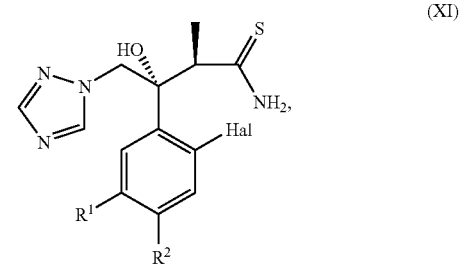

(XI)

wherein Hal, $R^1$ and $R^2$ have the same meaning as in formula (X), which is then reacted with 2-bromo-4'-cyano-acetophenone to give a compound of formula (XII):

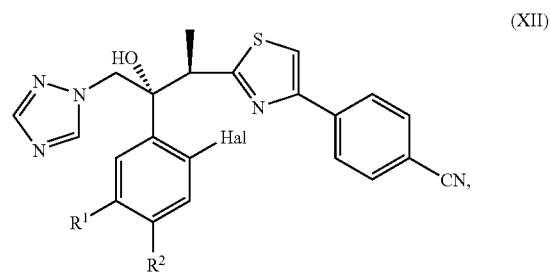

(XII)

wherein Hal, $R^1$ and $R^2$ have the same meaning as in formula (XI).

Suitable parameters for the aforementioned reaction steps are in more detail described, for example, in WO99/45008. The compound of the formula (X) is reacted with dithiophosphoric acid O,O-diethyl ester and water or dithiophosphoric acid O,O-diethyl ester, water and isopropanol, e.g. at a temperature between 90° C. and 150° C. for 4 to 8 hr. to give the compound of the formula (XI), followed by reacting said compound with the 2-bromo-4'-cyanoacetophenone at a temperature between room temperature and about 80° C. in acetonitrile, ethanol or methanol, e.g. for 2 to 24 hours to give the compound of the formula (XII). If desired, salt formation by known procedures may follow. Hydrates or solvates with pharmaceutically acceptable solvents such as ethanol can also be obtained, for example, during crystallization.

A preferred specific embodiment of the present invention is the use of the process according to the present invention in the manufacture of a compound of formula (XII-a)

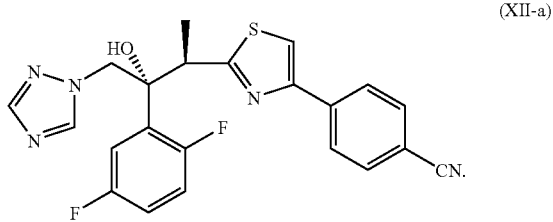

(XII-a)

or a pharmaceutically acceptable salt, hydrate of solvate thereof;

The following Examples serve to illustrate the invention without limiting the scope thereof in any particular.

EXAMPLE 1

(2S)-1-(2,5-Difluoro-phenyl)-2-(tetrahydro-pyran-2-yloxy)-propan-1-one 1,4-Difluorobenzene (1.8 g; 15.8 mmol) and (2S)-1-Morpholin-4-yl-2-(tetrahydro-pyran-2-yloxy)-propan-1-one (3 g; 10.5 mmol) are dissolved in dry THF (15 ml). The mixture is cooled to 0° C. and then lithium diisopropylamine (7.9 ml of a 2M solution in THF/Heptane; 15.8 mmol) is added dropwise over a period of 20 minutes. The mixture is stirred for another 2 hours at 0° C. The reaction is then quenched with a saturated ammonium chloride solution. The reaction mixture is extracted with ethyl acetate. The organic phase is washed with water and brine and then dried over magnesium sulfate. The solids are filtered off and the solvent is removed under reduced pressure. The crude product is chromatographed over silicagel (eluent:Petrol ether/Ethyl acetate 50:1 to 30:1). 1.31 g of yellow crystalline material (yield 44.8%) is obtained with a HPLC purity of 96.2%.

NMR: (CDCl$_3$; 400 MHz): 7.53-7.47 (m; 1H); 7.24-7.16 (m; 1H); 7.15-7.07 (m; 1H); 5.10 (qd; J=7.2 Hz; 2.0 Hz; ½H); 4.85 (q; J=7.2 Hz; ½H); 4.74 (m; ½H); 4.64 (m; ½H); 3.89 (m; ½H); 3.71 (m; ½H); 3.51 (m; ½H); 3.34 (m; ½H); 1.90-1.48 (m; 6H); 1.47 (d; J=7.2 Hz; 1.5H); 1.42 (d; J=7.2 Hz; 1.5H).

EXAMPLE 2

1(S)-[2-(2,5-Difluoro-phenyl)-1-methyl-allyloxy]-tetrahydro-pyran

Methyl triphenylphosphonium iodide (11.1 g; 27.7 mmol) was suspended in dry THF (100 ml). The reaction mixture is cooled in an ice bath. A sodium bis(trimethylsilyl)amid solution (30 ml of a 1M solution in THF) is added at such a rate to keep the temperature below 20° C. The reaction mixture was stirred for 3 hours at 15° C. then was cooled at −78° C. Then (2S)-1-(2,5-Difluoro-phenyl)-2-(tetrahydro-pyran-2-yloxy)-propan-1-one (5.0 g; 15.7 mmol in solution in THF (20 ml)) is added to the previous mixture at such a rate to keep the temperature below −70° C. The mixture is stirred 5 minutes at this temperature then for 17 hours at 10° C.

Then ethyl acetate (5 ml) and hexanes (350 ml) was added. The suspension was stirred for 15 minutes (precipitation of triphenylphosphine-oxide). The solids were filtered off. The filter-cake was washed with hexane (60 ml). The filtrate is washed twice with a 1:1 water methanol mixture (2 times 100 ml) and with brine (100 ml). The organic phase is dried over magnesium sulfate. The solids are filtered off and the solvent is removed under reduced pressure. The crude product is chromatographed over silicagel (eluent:Petrol ether/Ethyl acetate 20:1 to 10:1). 3.45 g of a colorless oil (yield 69%) is obtained with a HPLC purity of 99.9% and ee is 99.2%.

NMR: (CDCl$_3$; 400 MHz): 7.02-6.94 (m; 3H); 5.58 (s; 1H); 5.23 (s; 1H); 4.76 (m; 1H); 4.66 (q; J=7.2 Hz; 1H); 3.94 (m; 1H); 3.55 (m; 1H); 1.90-1.48 (m; 6H); 1.27 (d; J=7.2 Hz; 3H).

EXAMPLE 3

2(S)-3-(2,5-Difluoro-phenyl)-but-3-en-2-ol

1(S)-[2-(2,5-Difluoro-phenyl)-1-methyl-allyloxy]-4-tetrahydro-pyran (5.79 g; 20.4 mmol)) was dissolved in methanol (40 ml). Pyridinium toluene sulfonate (2.61 g; 10.4 mmol) is added and the mixture is stirred at 35° C. for 12 hours. The solvent was removed under reduced pressure. The residue was taken up in ethyl acetate (40 ml) and the solids are filtered off. The crude product is chromatographed over silicagel (eluent:Petrol ether/Ethyl acetate 200:1 to 50:1). 3.45 g of a yellow oil (yield 81.4%) is obtained with a HPLC purity of 99.9%; ee: 99.2%.

NMR: (DMSO D6; 400 MHz): 7.27-7.13 (m; 3H); 5.50 (sbr; 1H); 5.14 (sbr; 1H); 5.12 (d; J=4.8 Hz; OH); 4.51 (m; 1H); 1.06 (d; J=6.8 Hz; 3H).

EXAMPLE 4

1(R)-[2(S)-(2,5-Difluoro-phenyl)-oxiranyl]-ethanol

L-(+)-Diethyl tartrate (7.9 g; 38.2 mmol) is dissolved in dry methylene chloride (250 ml) at −30° C. and molecular sieves 4A are added (8 g). Titanium tetraisopropoxide (TIPO) (10.8 g; 36.5 mmol) is added to the mixture. The mixture is stirred 1 hour at −30° C. Then 2(S)-3-(2,5-Difluoro-phenyl)-but-3-en-2-ol (7 g; 33.2 mmol) dissolved in dry methylene chloride (50 ml) is added slowly. The mixture is stirred one hour −30° C. then Tert-butyl hydroperoxide (TBHP) (13.2 ml of a 5.5M solution in decane; 73.1 mmol) is added dropwise at −25° C. The mixture is stirred 12 hours at −25° C. The reaction mixture is warmed up to 10° C. and an aqueous solution of ferrous sulfate (18 g) and tartaric acid (18 g) in water (300 ml) is added. The mixture is stirred at 10° C. for 30 minutes. The phases are separated and the aqueous phase is extracted 3 times with methylene chloride (3 times 250 ml). To the combined organic phases a 1M aqueous sodium hydroxide solution (100 ml) is added and the mixture is stirred for one hour. The phases are separated and the aqueous phase is extracted twice with methylene chloride (2 times 50 ml). The organic phase is dried over magnesium sulfate. The solids are filtered off and the solvent is removed under reduced pressure. The crude product is chromatographed over silicagel (eluent:Petrol ether/Ethyl acetate 20:1). 6.55 g of a light yellow oil (yield 82%) is obtained with a HPLC purity of 82%.

NMR: (CDCl$_3$; 400 MHz): 7.12-7.10 (m; 1H); 7.09-6.98 (m; 2H); 4.12 (m(br); 1H); 3.28 (d; J=4.8 Hz; 1H); 2.91 (d; J=4.8 Hz; 1H); 2.28 (d(br); OH); 1.23 (d; J=6.5 Hz; 3H).

EXAMPLE 5

1(S)-[2(S)-(2,5-Difluoro-phenyl)-oxiranyl]-ethanol

1(R)-[2(S)-(2,5-Difluoro-phenyl)-oxiranyl]-ethanol (500 mg; 2.34 mmol; HPLC purity 93%) is dissolved in dry methylene chloride (25 ml). Dry pyridine (0.38 ml; 4.67 mmol) is added and the reaction mixture is cooled to 0° C. Then trifluoromethanesulfonic anhydride (0.88 ml; 5.14 mmol) is added dropwise. The reaction mixture is stirred at 0° C. for 15 minutes. Then 5 drops of 5% aqueous sulfuric acid and water (5 ml) is added and the phases are separated. The aqueous layer is extracted 3 times with ethyl acetate (3 times 20 ml). The combined organic phases are first washed with 2M aqueous hydrochloric acid solution (20 ml), with a saturated bicarbonate solution (20 ml) and finally with brine (20 ml). The organic phase is dried over magnesium sulfate. The solids are filtered off and the solvent is removed under reduced pressure.

The obtained crude oil (0.766 g) is used as is for the following transformation.

NMR: (CDCl$_3$; 400 MHz): 7.17-7.12 (m; 1H); 7.11-7.06 (m; 2H); 5.18 (q; J=6.6 Hz; 1H); 3.23 (d; J=4.5 Hz; 1H); 2.97 (d; J=4.5 Hz; 1H); 1.51 (d; J=6.6 Hz; 3H).

The previously prepared triflate (766 mg; 2.31 mmol) is dissolved in DMF (20 ml distilled prior to use). Potassium nitrite (981 mg; 11.5 mmol) and 18-Crown-6-ether (37 mg; 0.14 mmol) are added and the mixture is stirred at 18° C. for half an hour. The reaction mixture is diluted with ethanol (5 ml). Sodium hydroxide (138 mg; 3.46 mmol) and water (5 ml) is added. The mixture is stirred at 18° C. for one hour. The reaction mixture is extracted 3 times with ethyl acetate (3 times 20 ml). The combined organic phases are first washed with brine (10 ml). The organic phase is dried over magnesium sulfate. The solids are filtered off and the solvent is removed under reduced pressure. The residue is chromatographed over silicagel (eluent: Petrolether/Ethyl acetate: 20:1). 305 mg of a light yellow oil (yield: 65%) is obtained NMR: (CDCl$_3$; 400 MHz): 7.16-7.12 (m; 1H); 7.05-6.97 (m; 2H); 4.17 (m(br); 1H; 3.33 (d; J=4.8 Hz; 1H); 2.80 (d=4.8 Hz; 1H); 1.87 (d(br); OH; 1.17 (d; J=6.5 Hz; 3H).

EXAMPLE 6

(2R,3R)-2-(2,5-Difluoro-phenyl)-1-[1,2,4]-triazol-1-yl-butane-2,3-diol 1,2,4-Triazole (274 mg; 3.89 mmol) is dissolved in DMSO (3 ml). Sodium hydride (124 mg; 60% suspension in paraffin; 3.24 mmol) is added and the reaction mixture is heated to 70° C. for one hour. The reaction mixture is cooled to room temperature and 1(S)-[2(S)-(2,5-Difluoro-phenyl)-oxiranyl]-ethanol (275 mg; 1.3 mmol) dissolved in DMSO (2 ml) is added slowly over a period of 10 minutes. The reaction mixture is then heated to 70° C. for three hours. The solvent is evaporated. The residue is taken-up in ethyl acetate (10 ml) and water (5 ml). The phases are separated. The aqueous layer is extracted 3 times with ethyl acetate (3 times 5 ml). The combined organic phases are washed twice with water (2 times 5 ml). The organic phase is dried over sodium sulfate. The solids are filtered off and the solvent is removed under reduced pressure. The crude product is dissolved in ethyl acetate (16 ml). Oxalic acid (164 mg; 1.3 mmol) is added and the solution is stirred for 30 minutes. The mixture is stored at 0° C. overnight. The crystalline (2R,3R)-2-(2,5-Difluoro-phenyl)-1-[1,2,4]triazol-1-yl-butane-2,3-diol oxalate salt is filtered off. The crystals are washed with hexanes and dried under vacuum. The desired compound is obtained as a white powder (337 mg); yield 66.7% with an optical purity higher than 95% (no other isomer is visible in NMR).

NMR: (DMSO D6; 400 MHz): 8.32 (s; 1H), 7.61 (s; 1H); 7.13 (m; 1H); 7.07 (m; 1H); 6.93 (m; 1H); 5.55 (s(br); 2H OH, NH); 4.70 (s; 2H); 4.22 (m(br); 1H); 0.81 (d; J=6.5 Hz; 3H).

EXAMPLE 7

(2(R),3(S))-1-[2-(2,5-Difluoro-phenyl)-3-methyl-oxiranylmethyl]-1H-[1,2,4]triazole (2R,3R)-2-(2,5-Difluoro-phenyl)-1-[1,2,4]-triazol-1-yl-butane-2,3-diol (324 mg; 1.20 mmol) is dissolved in methylene chloride (13 ml). Triethylamine (0.59 ml; 4.2 mmol) is added to the reaction mixture. The reaction mixture is cooled to 0° C. and methane sulfonyl chloride (0.21 ml; 2.72 mmol) dissolved in methylene chloride (4 ml) is added. The reaction mixture is stirred 4 hours at 0° C. Then a 6M aqueous sodium hydroxide solution (0.98 ml) is added. The reaction mixture is stirred at room temperature overnight. The solvent is evaporated. The residue is taken-up in ethyl acetate (15 ml) and water (8 ml). The phases are separated. The aqueous layer is extracted 3 times with ethyl acetate (3 times 10 ml). The combined organic phases are washed twice with water (2 times 5 ml). The organic phase is dried over sodium sulfate. The solids are filtered off and the solvent is removed under reduced pressure. The crude compound is chromatographed (eluent:Ethyl acetate/Petrol ether 1:2) and desired compound is obtained as white crystals (116 mg); yield 38.5%.

HPLC purity: 99.5% ee: 99.99%

NMR: (CDCl$_3$; 400 MHz): 7.98 (s; 1H); 7.73 (s; 1H); 7.00-6.88 (m; 2H); 6.77 (m; 1H); 4.97 (d; J=14.5 Hz; 1H); 4.41 (d; J=14.5 Hz; 1H); 3.19 (q; J=5.6 Hz; 1H); 1.64 (d; J=5.6 Hz; 3H).

EXAMPLE 8

1(S)-[2(S)-(2,5-Difluoro-phenyl)-oxiranyl]-ethanol

DEAD (870 mg; 2 mmol) and p-nitrobenzoic acid (337 mg; 2 mmol) were dissolved in dry THF (3 ml) and the solution was cooled to 0° C. Then 1(R)-[2(S)-2,5-Difluoro-phenyl)-oxiranyl]-ethanol (100 mg; 0.5 mmol) and triphenylphosphine (524 mg; 2 mmol) is dissolved in dry THF (10 ml) were added dropwise at such a rate to maintain the temperature below 10° C. The mixture was then allowed to react to completion at 20° C. for 20 hours. Half of the solvent was removed under reduced pressure. The reaction mixture is diluted with diethyl ether (80 ml) and washed with an aqueous saturated ammonium chloride solution. The organic phase is dried over magnesium sulfate. The solids are filtered off and the solvent is removed under reduced pressure. The residue is dissolved in methanol (25 ml) and treated with potassium carbonate (450 mg). The reaction mixture is diluted with an aqueous saturated ammonium chloride solution (30 ml). The reaction mixture is extracted with ethyl acetate (2 times 20 ml). The combined organic phases are washed with water (2 times 30 ml) and with brine (2 times 30 ml). The organic phase is dried over magnesium sulfate. The solids are filtered off and the solvent is removed under reduced pressure. The crude residue is purified by chromatography (Petrole ether/ ethyl acetate 20:1). 53 mg (yield: 53%) of desired 1 (S)-[2 (S)-(2,5-Difluoro-phenyl)-oxiranyl]-ethanol was obtained as a colorless oil. The HPLC purity is 76%.

A small portion is converted to the triazolo-diol derivative in order to determine the enantiospecificity of the reaction.

EXAMPLE 9

(2R,3R)-2-(2,5-Difluoro-phenyl)-1-[1,2,4]-triazol-1-yl-butane-2,3-diol 1,2,4-Triazole (7 mg; 0.1 mmol) is dissolved in DMF (0.5 ml). Sodium hydride (4.4 mg; 60% suspension in paraffin; 0.1 mmol) is added and the reaction mixture is heated to 70° C. for one hour. The reaction mixture is cooled to room temperature and 1(S)-[2(S)-(2,5-Difluoro-phenyl)-oxiranyl]-ethanol (5 mg; 0.025 mmol from example 8) dissolved in DMF (0.5 ml) is added slowly. The reaction mixture is then heated to 70° C. for three hours. The solvent is evaporated. The residue is taken-up in ethyl acetate (5 ml) and water (3 ml). The phases are separated. The aqueous layer is extracted 3 times with ethyl acetate (3 times 5 ml). The combined organic phases are washed twice with water (2 times 5 ml). The organic phase is dried over sodium sulfate. The solids are filtered off and the solvent is removed under reduced pressure. 5 mg of (2R,3R)-2-(2,5-Difluoro-phenyl)-1-[1,2,4]-triazol-1-yl-butane-2,3-diol are obtained as a light yellow oil.

This compound was analyzed by chiral HPLC. The diastereoisomeric excess was determined to be 94%.

What is claimed is:

1. A process for the preparation of a compound of formula (I)

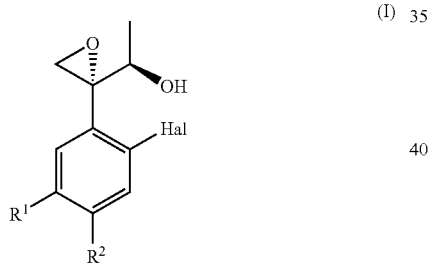

wherein
Hal represents fluoro or chloro and
$R^1$ and $R^2$ represent, independently from one another, hydrogen or one of the meanings of Hal;
in which process a compound of formula (II)

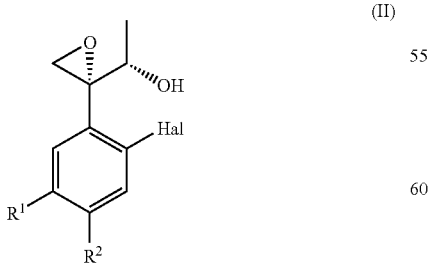

is converted to a corresponding alkyl, fluoroalkyl or aryl sulfonic acid ester, which is then reacted with an alkali metal nitrite in the presence of a suitable crown ether in a polar non-nucleophilic solvent at a temperature of −10 to 50° C. to give the compound of formula (I).

2. A process according to claim 1 wherein said fluoroalkyl sulfonic acid ester is the trifluoromethylsulfonic acid ester.

3. A process according to claim 1, wherein the alkali metal nitrite is sodium or potassium nitrite.

4. A process according to claim 1, wherein, in the event said nitrite is potassium nitrite, the crown ether is the 18-crown-6 ether, in the event said nitrite is sodium nitrite, said crown ether is 15-crown-3-ether.

5. A process according to claim 3, wherein the alkali metal nitrite is potassium nitrite.

6. A process according to claim 1, wherein a solvent selected from the group consisting of dimethylsulfoxide, N,N-dimethylformamide, 1,3-dimethyl-3,4,5,6-tetrahydro-2 (1H) -pyrimidinone, tetrahydrofurane, dioxane, formamide and mixtures thereof is used as the polar non-nucleophilic solvent.

7. A process according to claim 1, wherein, in formula (I), Hal represents fluoro and one of $R^1$ and $R^2$ represents hydrogen and the other fluoro.

8. A process according to claim 7, wherein $R^1$ represents fluoro and $R^2$ represents hydrogen.

9. A process according to claim 8, wherein the compound of formula (II) is obtained by a process which includes the reaction of 1,4-difluorobenzene with a compound of formula (III)

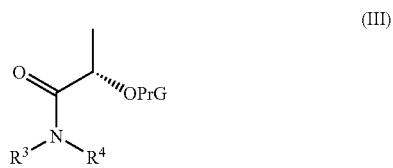

wherein
PrG represents a hydroxyl-protecting group,
$R^3$ represents methyl or ethyl, and
$R^4$ represents methyl, ethyl or methoxy, or
$R^3$ and $R^4$ taken together with the nitrogen atom to which they are bound represent a 4-to 6-membered heterocyclic group having from 0 to 2 additional heteroatoms selected from nitrogen or oxygen; in the presence of a base, to yield a compound of formula (IV)

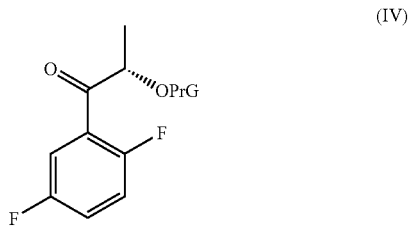

wherein PrG has the same meaning as in Formula (III).

10. A process according to claim 1, wherein the compound of formula (II) is obtained by a process which includes reacting a compound of formula (V)

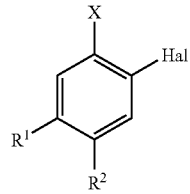
(V)

wherein
  Hal represents fluoro or chloro,
  X represents iodo or bromo, and
  $R^1$ and $R^2$ represent, independently from one another, hydrogen, fluoro or chloro;
with magnesium, and the obtained product is reacted with a compound of formula (III)

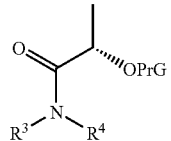
(III)

wherein
  PrG represents a hydroxyl-protecting group,
  $R^3$ represents methyl or ethyl, and
  $R^4$ represents methyl, ethyl or methoxy, or
  $R^3$ and $R^4$ taken together with the nitrogen atom to which they are bound represent a 4-to 6-membered heterocyclic group having from 0 to 2 additional heteroatoms selected from nitrogen or oxygen;
to yield a compound of formula (VI)

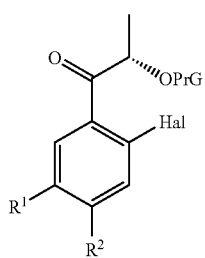
(VI)

wherein
  PrG has the same meaning as in formula (III) and
  $R^1$ and $R^2$ have the same meaning as in formula (V).

11. A process according to claim 9, wherein $R^3$ and $R^4$ taken together with the nitrogen atom to which they are bound represent a morpholin-4-yl residue.

12. A process according to claim 1 including the process step wherein the compound of formula (VI)

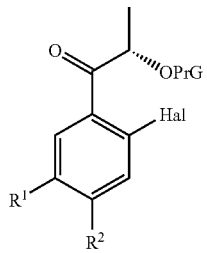
(VI)

wherein
  Hal, $R^1$ and $R^2$ have one of the meanings defined in claim 1, and PrG represents a hydroxyl-protecting group, is converted to a compound of formula (VII)

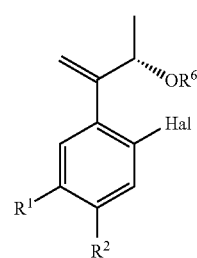
(VII)

wherein
  Hal, $R^1$ and $R^2$ have the same meaning as in formula (VI) and
  $R^6$ represents PrG or hydrogen.

13. A process according to claim 12, wherein the compound of formula (VII) is deprotected when $R^6$ represents a hydroxyl-protecting group PrG, and/or converted to the compound of formula (II) via Sharpless Epoxidation:

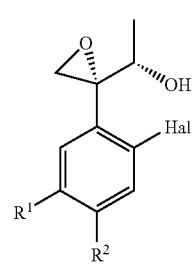
(II)

wherein
  Hal, $R^1$ and $R^2$ have the same meaning as in formula (VI).

14. A process according to claim 1 additionally including the further step of reacting said compound of formula (I) with 1,2,4-Triazole in the presence of a base to give a compound of formula (VIII)

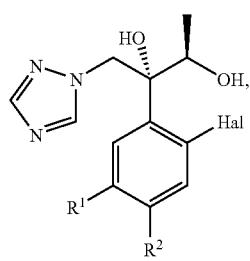

(VIII)

wherein Hal, $R^1$ and $R^2$ have the same meaning as in formula (I),
which compound is then converted to a compound of formula (IX):

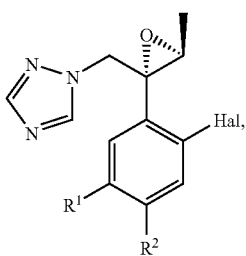

(IX)

wherein Hal, $R^1$ and $R^2$ have the same meaning as in formula (I).

15. A process according to claim 14 further including the steps of converting the compound of formula (IX) to a compound of formula (X)

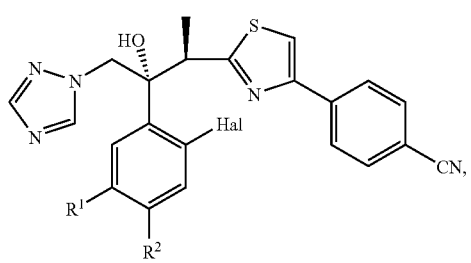

(X)

wherein Hal, $R^1$ and $R^2$ have the same meaning as in formula (IX), reacting said compound of formula (X) with dithiophosphoric acid O,O-diethyl ester or ammonium sulfide to give a compound of formula (XI):

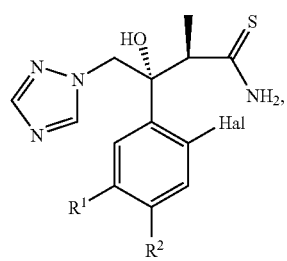

(XI)

wherein Hal, $R^1$ and $R^2$ have the same meaning as in formula (X), and further reacting said compound of formula (XI) with 2-bromo-4'-cyano-acetophenone to give a compound of formula (XII):

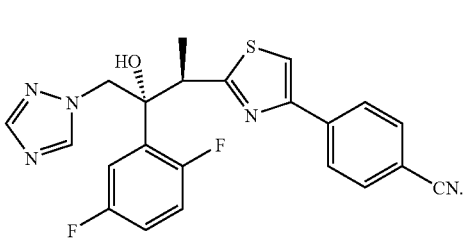

(XII)

wherein Hal, $R^1$ and $R^2$ have the same meaning as in formula (XI).

16. A process according to claim 15, wherein Hal, $R^1$ and $R^2$ are fluoro, fluoro and hydrogen, respectively and said compound has the formula (XII-a)

(XII-a)

17. A process according to claim 10, wherein $R^3$ and $R^4$ taken together with the nitrogen atom to which they are bound represent a morpholin-4-yl residue.

* * * * *